United States Patent [19]

May

[11] 4,126,127

[45] Nov. 21, 1978

[54] SUCTIONING/OXYGENATING LARYNGOSCOPE BLADE

[76] Inventor: Laurence M. May, Rte. 1, Box 214-A, Ponchatoula, La. 70454

[21] Appl. No.: 726,839

[22] Filed: Sep. 27, 1976

[51] Int. Cl.² ............................................. A61B 1/06
[52] U.S. Cl. .................................... 128/11; 128/13; 128/16; 128/276
[58] Field of Search ..................... 128/8, 9, 10, 11, 15, 128/145.8, 351, 276, 13, 16

[56] References Cited

U.S. PATENT DOCUMENTS

| | | | |
|---|---|---|---|
| 2,854,004 | 9/1958 | Durrant | 128/276 |
| 3,626,471 | 12/1971 | Florin | 128/276 |
| 3,794,026 | 2/1974 | Jacobs | 128/145.8 |
| 3,941,120 | 3/1976 | Lee | 128/4 |

Primary Examiner—Robert W. Michell
Assistant Examiner—Henry S. Layton
Attorney, Agent, or Firm—Llewellyn A. Proctor

[57] ABSTRACT

This laryngoscope blade comprises an illuminated, molded tongue retractor, wherein, as viewed by a patient, a suction conduit extends up the left side of the blade, from just short of the distal tip of the blade, to the proximal end of the blade, with means for attachment to a separate suction hose and vacuum pump. A flow of 100% oxygen is provided near the distal tip of the blade through a second conduit, smaller in diameter than the first, extending down the right side of the blade from the proximal end of the blade, with means for attachment to a separate oxygen delivery hose and oxygen source. The improved blade is uniquely shaped to facilitate endotracheal intubation, in a 100% oxygen environment, with high-volume suction immediately available, at the glottis, in the illuminated field of view.

9 Claims, 10 Drawing Figures 4,126,127

SUCTIONING/OXYGENATING LARYNGOSCOPE BLADE

SUMMARY OF THE INVENTION

The present invention relates generally to medical instruments, and has particular reference to an improved design of laryngoscope blade incorporating illumination, suction, and oxygen flow, for the purpose of facilitating medical procedures in the throat, especially endotracheal intubation.

A primary object of the invention is to provide a laryngoscope blade which is capable of rapidly removing large volumes of secretions, vomitus, or blood from the pharynx through suction ports located near the tip of the blade.

A further object of the invention is to provide a flow of one hundred percent oxygen near the tip of the blade.

A still further object of the invention is to provide illumination of the area at the tip of the blade so that the field of view is a focal area of illumination, suction, and oxygen. In use, when the tip of the blade is placed underneath the epiglottis, exposing the vocal cords to view, the suction ports and oxygen flow are directed to the glottis, thereby protecting the airway from aspiration and enhancing oxygenation of the patient.

An additional advantage, inherent in the blade design, is that the endoscopist is reminded to have functioning suction ready for use, before initiating endoscopy. In the present state of the art, this is too easily and frequently forgotten.

In the past, many designs of tongue depressors have been proposed. Many of these enable illuminated direct viewing of the area of the vocal cords and hence are termed laryngoscopes. The laryngoscope blade disclosed in U.S. Pat. No. 2,854,004 granted Sept. 30, 1958 to C. W. Durrant, provided suction at the tip of the blade. My blade differs from the above-named, and the rest of the prior art, as will be made clear in the following detailed description, referring by numerals to the accompanying drawings, in which like reference numbers designate the same parts in each of the views:

FIG. 1 is a diagram illustrating the use of the improved laryngoscope blade. Endotracheal intubation is usually performed with the patient supine and the head extended. Under direct vision the endotracheal tube (not shown) is placed through the patient's glottis 28 into the trachea 29. Once in place a balloon cuff on the endotracheal tube is inflated and the patient's airway is secure from aspirating down the trachea 29 into the lungs 30. Aspiration of gastric contents can lead to a severe pneumonia and death. Until the endotracheal tube is securely in position, rapid removal of vomitus, if present, is necessary to prevent aspiration; since, material regurgitated from the stomach 32, up the esophagus 31, into the pharynx 33, will spill into the trachea 29, if the liquid level exceeds the highth of the glottis 28.

DETAILED DESCRIPTION

Figure 1:
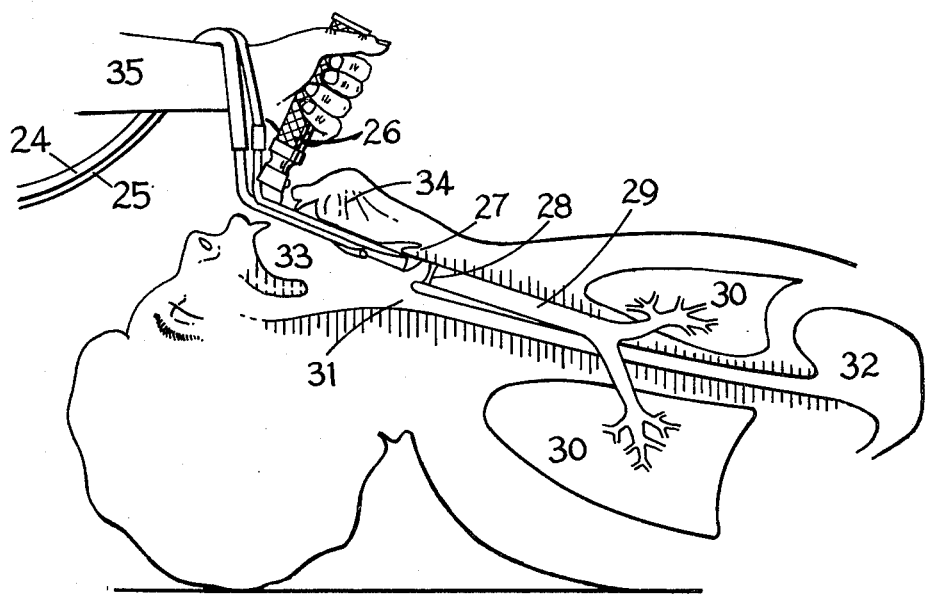
Figure 2:
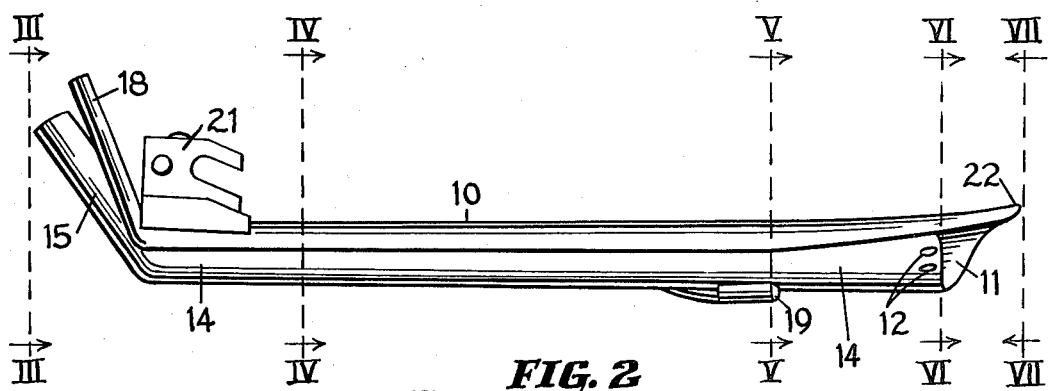
FIG. 2 is a right side elevation of an improved laryngoscope blade embodying the invention 10.
Figure 4:
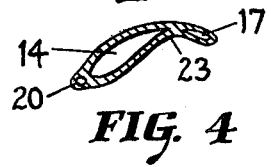
FIG. 4 is a cross-sectional view taken along lines IV—IV of FIG. 2.
Figures 5, 6:
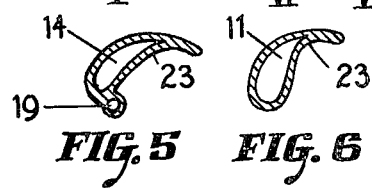
FIG. 5 is a cross-sectional view taken along lines V—V of FIG. 2.
FIG. 6 is a cross-sectional view taken along lines VI—VI of FIG. 2.
Figure 3:
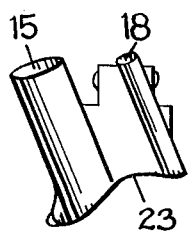
FIG. 3 is an end view taken along lines III—III of FIG. 2.
Figure 7:
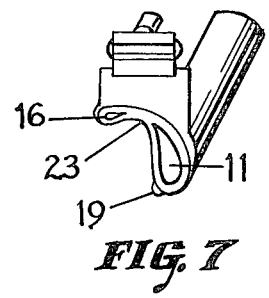
FIG. 7 is an end view taken along lines VII—VII of FIG. 2.
Figure 8:
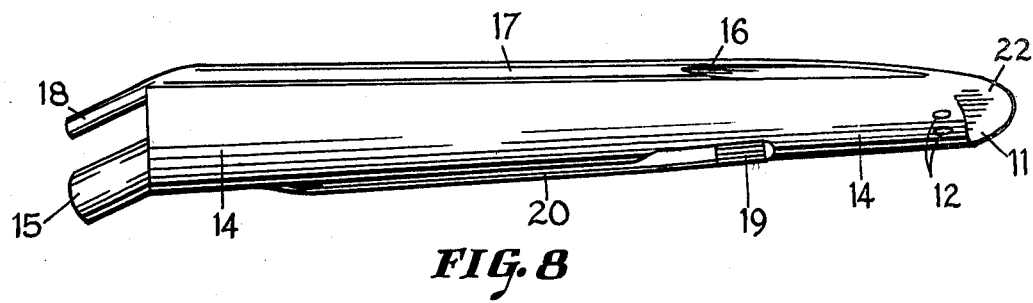
FIG. 8 is a bottom plan view of the blade.
Figure 9:
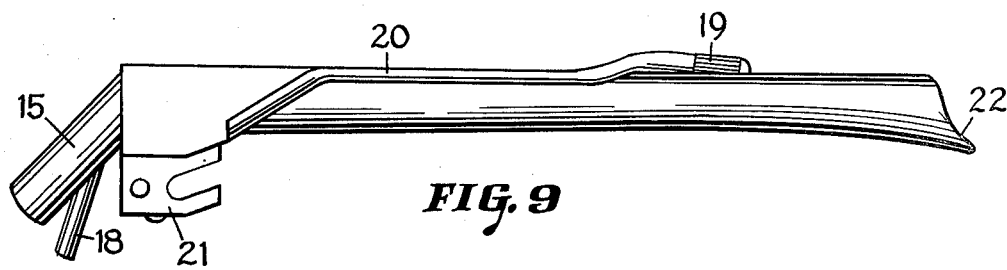
FIG. 9 is a left side elevation of the blade taken from the side opposite from FIG. 2.
Figure 10:
FIG. 10 is a top plan view of the blade.

In the present invention 10, referring to FIG. 2, the suction tube element 14 of the blade extends lengthwise down the left side of the blade (viewed by a patient), and corresponds to the vertical flange of other laryngoscope blades; that both provides structural strength, and holds the patient's tongue 34 retracted to the left side of the mouth. Cross-sectional views, FIGS. 4, 5, reveal a suction conduit 14, essentially tear-drop in shape, that tapers into the transverse arch of the blade, under which is the sighting channel 23.

Referring to FIGS. 1, 2, 6, 8, the placement of the main suction port 11, and optional additional suction ports 12, just short of the tip 22 of the blade, does not favor suctioning-up soft tissues, such as the epiglottis 27, nor is a suction head incorporated in the design, in distinction to the Durrant blade. Suction port placement 11,12 immediately guards the area of the vocal cords 28, when they are exposed to view, under direct vision. No illuminated laryngoscope blade in the prior art has provided this feature.

In cross-section, the lumens of both the main suction port 11, and the suction conduit 14 extending down the blade, are of a large cross-sectional area, approximately 0.076 square inches. Maximal laminar flow of liquid is promoted by this design, which is approximately equal in internal cross-sectional area to the rubber suction hose 24 (internal diameter 5/16 inch) to which it is attached at 15. By comparison, the metal or plastic Yankauer tonsil suction handle (not shown), used by many anesthetists, reduces the efficiency of the suction hose 24 by approximately thirty-three percent. Yankauer suction design has small ports that offer resistance to flow and produce turbulence. Unimpeded, smooth laminar flow is the most efficient method to transport a liquid flowing through a tube, such as that featured in the present design. Volume removal is limited by the cross-sectional area of the suction conduit and the amount of negative pressure applied to the conduit. A prototype blade of the present design 10, has been measured to remove fifteen hundred milliliters of liquid in fifteen seconds. This did not represent a reduction in volume efficiency compared to the suction hose 24 alone.

The laryngoscope suction element attaches at 15 to portable or wall vacuum device, not considered part of the present invention, by means of a rubber hose 24 previously mentioned. In use, in endoscopy for endotracheal intubation, the laryngoscope is held in the endoscopist's left hand, and the blade 10 is introduced into the patient's mouth 33, with the suction in the OFF position. Suction is only turned ON if required. OFF-/ON is controlled with compression by the endoscopist's foot — standing on, or removed from standing on, the rubber suction hose 24. In this manner, blood or secretions may be suctioned away as the blade is advanced into the patient's mouth 33. If the patient vomits, suction is immediately available at the glottis 28 protecting the patient's airway. Since the anesthetist need not reach for a separate suction, he is free to progress with endotracheal intubation with his right hand. This high-volume suction feature of the present design is considered especially valuable when endoscopy is necessary in the patient with a full stomach 32 — a situation frequently encountered in anesthetic practice.

Through an oxygen port 16, near the tip of the blade, one hundred percent oxygen is provided to the posterior pharynx through a small lumen conduit 17, that extends lengthwise down the right side of the blade (viewed by a patient). High oxygen flows are achievable, but flows of two to fifteen liters per minute should be sufficient, unless suctioning is being performed — in which case oxygen flow should be increased, if possible. The venturi principle of entrainment of a second gas is not utilized since dilution of the oxygen concentration in the mouth is not desirable, especially when employing the Apneic Oxygenation technique, known in the art. The Rapid Induction/Apneic Oxygenation technique consists of oxygenation/denitrogenation of the patient with one hundred percent oxygen by mask for ten to twenty minutes, utilizing an anesthesia machine or similar device, then rapidly inducing narcosis and paralysis with intravenously administered thiobarbiturate (Sodium Pentothal) and muscle relaxant (Succinylcholine). A flow of one hundred percent oxygen is then provided to the posterior pharynx 33 — in the prior art by means of a nasal cannula. With one hundred percent oxygen in the pharynx 33, oxygen flow up the trachea 29 from the lungs 30 to the pharynx 33 does not occur, but flow in the opposite direction will occur if a concentration gradient developes. This technique allows for fifteen minutes for endoscopy, except in the moribund patient, without the patient breathing or becoming hypoxemic. This is of great advantage in endoscopy when the anatomical structure of the patient makes intubation difficult and not readily performed. Although previous laryngoscope blades have provided oxygen, their designs are limiting and prohibitive of the present proposed application. These previous oxygenating laryngoscope blades are of a tubular shape termed Suspension laryngoscope blades, for use by the E.N.T. surgeon, which do not facilitate endotracheal intubation, nor do they provide a one hundred percent concentration of oxygen to the posterior pharynx, because of entrainment of room air into the oxygen stream. The present invention is the first laryngoscope blade which supplies one hundred percent oxygen to the posterior pharynx and facilitates endotracheal intubation, in combination.

The blade 10, is connected at 18 to green oxygen delivery tubing 25, known in the art, to a portable oxygen unit, wall oxygen supply, or an anesthesia machine, not considered part of the present invention. When the invention is held for use, tubing 24 and 25 hangs over the endoscopist's left wrist 35, out of the field of view.

The blade may be constructed straight or with some amount of curve. The prototype design 10 is that of a predominantly straight blade, approximately seven inches in length, with the leading one inch of the tip of the blade 22 upturned slightly (viewed by a patient). The blade may be constructed in different sizes for different size patients, such as children. However, the adult blade size 10, should be of use in a wide range of adults and children.

The blade 10 may be constructed in metal, or some other material, such as plastic, or combinations of materials, which provides sufficient structural strength.

The illumination 19 of the blade, wiring 20, and the battery-containing laryngoscope handle 26, to which the blade 10 pivotally attaches at 21, is provided in a manner described in the prior art, such as that disclosed in U.S. Pat. No. 2,433,705 granted Dec. 30, 1947 to H. E. Palmeter. Alternatively, the illumination could be transmitted by a fiberoptic bundle — known in the prior art, not depicted in the drawings, and not considered crucial to the present design; but is mentioned to illustrate that a variation of the method of illumination of the proposed suctioning/oxygenating laryngoscope blade, is not to be considered a departure from the spirit of the present design. The method of illumination of the blade, and its exact spatial arrangement, is subject to change with developemental improvement of the invention.

Having fully described my invention, it is to be understood that I am not to be limited to the details herein set forth but that my invention is of the full scope of the appended claims.

I claim:

1. In apparatus embodying an illuminated, transversely arched laryngoscope blade, shaped to facilitate rapid endotracheal inturbation of a patient, the improvement wherein there is included within the transverse arch of said blade a pair of lumens formed inside the wall forming said blade and constituting an integral part of said blade, a first lumen extending lengthwise from the proximate end at which an oxygen inlet attachment means is provided, through an edge of said blade and ending at a port located at the distal end of said blade to provide a conduit for delivering essentially pure oxygen to the posterior pharnx of the patient, and a second lumen extending lengthwise from the proximate end at which a suction inlet attachment means is provided, through the opposite edge of said blade to a port at the tip of the blade which provides a suction conduit for the removal of fluids as the blade is advanced into the patients mouth and beyond, as during endotracheal inturbation of a patient.

2. The apparatus of claim 1 wherein the lumen which carries the oxygen extends down the right side of the blade.

3. The apparatus of claim 1 wherein the lumen which acts as a suction conduit is of cross-section essentially tear drop in shape, and tapers into the transverse arch of the blade which provides a sighting channel.

4. The apparatus of claim 1 wherein the lumen which acts as a suction conduit and the port at the tip of the blade which provides an inlet to the lumen which acts as a suction conduit are both of cross-section essentially tear drop in shape, and tapers into the transverse arch of the blade which provides a sighting channel.

5. The apparatus of claim 4 wherein the port at the tip of the blade constitutes the main suction port, and additional suction ports are provided just short of the tip of the blade.

6. The apparatus of claim 1 wherein the lumen which carries the oxygen is of relatively small cross-sectional area in relation to the cross-sectional area of the lumen which acts as a suction conduit, and the latter is of cross-section essentially tear drop in shape throughout its length, and tapers into the transverse arch of the blade which provides a sighting channel.

7. The apparatus of claim 1 wherein the blade is substantially straight from its proximate to its distal ends, with the distal end thereof being slightly upturned.

8. The apparatus of claim 1 wherein the oxygen inlet attachment means and suction inlet attachment means are adopted to accomodate hose connections, an oxygen delivery hose for connection to an oxygen source, and a suction hose for connection to a vacuum pump, the suction hose accomodated by the suction inlet attachment means being of cross-sectional area approximately equal to that of the lumen which acts as a suction conduit.

9. The apparatus of claim 1 wherein the illumination is provided by a light source mounted upon the surface of the blade, the illuminating source of which is located in the proximity of the transverse arch, the light source being powered by a battery located in a handle, pivotally attachable upon the proximate end of the blade.

* * * * *